United States Patent [19]

Russell

[11] Patent Number: 4,612,382

[45] Date of Patent: Sep. 16, 1986

[54] PREPARATION OF TRIETHYL DIMETHYL SILOXALANE

[75] Inventor: Charles G. Russell, Kingston, Canada

[73] Assignee: Du Pont Canada Inc., Mississauga, Canada

[21] Appl. No.: 625,226

[22] Filed: Jun. 27, 1984

[30] Foreign Application Priority Data

Jul. 5, 1983 [GB] United Kingdom ................. 8318207

[51] Int. Cl.$^4$ ............................................... C07F 5/06
[52] U.S. Cl. ..................................................... 556/173
[58] Field of Search ..................... 260/448 A; 556/173

[56] References Cited

U.S. PATENT DOCUMENTS

| 2,897,220 | 7/1959 | Jenkner | 260/448 A |
| 3,657,159 | 4/1972 | Vandenberg | 260/448 A X |
| 3,711,305 | 1/1973 | Anderson | 260/448 A X |
| 3,787,323 | 1/1974 | Aishima et al. | 526/127 X |
| 3,969,332 | 7/1976 | Gloriod et al. | 562/127 |
| 4,036,867 | 7/1977 | Piekarski et al. | 260/448 A |
| 4,324,877 | 4/1982 | Ueno et al. | 526/127 |

Primary Examiner—Helen M. S. Sneed

[57] ABSTRACT

A process for the preparation of triethyl dimethyl siloxalane is disclosed. The process comprises admixing octamethylcyclotetrasiloxane with triethyl aluminum, optionally in the presence of an inert hydrocarbon solvent, at a temperature of 170°–250° C. for a period of at least 10 minutes. The molar ratio of triethyl aluminum to octamethylcyclotetrasiloxane is at least 3.9:1 and preferably 3.9–4.5:1. The siloxalane may be used as a co-catalyst in the polymerization of ethylene and/or other alpha-olefins.

7 Claims, No Drawings

PREPARATION OF TRIETHYL DIMETHYL SILOXALANE

BACKGROUND OF THE INVENTION

1. Field of the Invention

The present invention relates to the preparation of triethyl dimethyl siloxalane and in particular to the preparation of such a siloxalane from octamethylcyclotetrasiloxane and triethylaluminum.

2. Description of the Prior Art

Alkyl siloxalanes have a variety of uses, including use as a co-catalyst in the polymerization of ethylene and/or other alpha-olefins, as is described in the copending patent application of M. A. Hamilton, D. A. Harbourne, R. Mulhaupt, C. G. Russell and V. G. Zboril, Ser. No. 625,225, filed concurrently herewith and in U.S. Pat. No. 3,969,332 of P. Gloriod et al., issued July 13, 1976.

The preparation of admixtures of triorganosilanes and organosiloxalanes by reacting hexaorganosiloxanes with alkyl aluminum compounds has been described by H. Jenkner in U.S. Pat. No. 2,897,220, issued July 29, 1959. The reaction of octamethylcyclotetrasiloxane and triethyl aluminum to give the ring-opened product $(C_2H_5)(CH_3)_2SiO[(CH_3)_2SiO]_2(CH_3)_2SiOAl(C_2H_5)_2$ has been described by H. Jenkner in Zeitschrift fuer Naturforschung 1959 Vol B, p. 133-134.

The preparation of triethyl dimethyl siloxalane by reacting octamethylcyclotetrasiloxane with triethyl aluminum at 50° C. for is described in the aforementioned U.S. Pat. No. 3,969,332. However, as shown hereinafter in the examples, it is believed that octamethylcyclotetrasiloxane and triethyl aluminum do not react at 50° C. to give triethyl dimethyl siloxalane.

A method for the preparation of triethyl dimethyl siloxalane has now been found.

SUMMARY OF THE INVENTION

Accordingly, the present invention provides a process for the preparation of triethyl dimethyl siloxalane comprising the step of admixing octamethylcyclotetrasiloxane with triethyl aluminum at a temperature of 170°–250° C. for a period of at least 10 minutes, the molar ratio of triethyl aluminum to octamethylcyclotetrasiloxane being at least 3.9:1.

In a preferred embodiment of the process of the present invention, the molar ratio of triethyl aluminum to octamethylcyclotetrasiloxane is in the range 3.9–4.5:1.

DETAILED DESCRIPTION OF THE INVENTION

The reactants for the process of the present invention viz. octamethylcyclotetrasiloxane and triethyl aluminum, may be admixed in the absence of solvent or one or both of the reactants may be in the form of solutions in inert hydrocarbon solvent. Preferably the same inert hydrocarbon solvent is used if both reactants are in the form of solutions. Moreover any such solvent may depend on the intended use for the triethyl dimethyl siloxalane obtained in the process of the present invention. For instance, if the siloxalane is to be used as a cocatalyst in the polymerization of alpha-olefins, the solvent must be compatible with and preferably be the same as the solvent in the polymerization process. In particular the solvent must not cause detrimental effects on the polymerization process. Such solvents are known and include for example, hexane, heptane, octane, cyclohexane, methylcyclohexane and hydrogenation naphtha.

In the process, triethyl aluminum is admixed with octamethylcyclotetrasiloxane. The reactants are admixed so that the molar ratio of triethyl aluminum to octamethylcyclotetrasiloxane is at least about 3.9:1 and preferably in the range of from about 3.9 to about 4.5:1, especially approximately 4.0:1. The concentrations of the solutions may be varied over a wide range and are primarily governed by practical considerations. For instance, the reactants may be admixed in the absence of organic solvent, or one or both reactants may be in the form of solutions in inert hydrocarbon solvents. The concentrations of any such solutions may be varied over a wide range, practical considerations being an important factor in determining the concentrations of any such solutions.

As is illustrated hereinafter in the examples, it is important to maintain the admixture of reactants at a temperature of from about 170° to about 250° C. This may be accomplished by, in particular, admixing the reactants at a temperature of less than about 170° C. and subsequently heating the admixture to a temperature in the range of from about 170° to about 250° C. The temperature should be maintained in the range of from about 170° to about 250° C. for a period of at least about 10 minutes and preferably from about 20 to about 120 minutes. Preferably the temperature is in the range of from about 180° to about 200° C.

The process of the present invention may be operated as a batch process or as a continuous process. If the process is a continuous process, the product of the reaction may be fed directly to another process e.g. a process for the manufacture of catalyst for an olefin polymerization process or to such a polymerization process per se.

As described above, the process of the present invention is directed to the manufacture of triethyl dimethyl siloxalane. That compound may, on the basis of nuclear magnetic resonance (NMR) spectroscopy, isomerize in solution and thus the product of the process may be a mixture of the isomers of triethyl dimethyl siloxalane. The isomers likely include $(C_2H_5)(CH_3)_2SiOAl(C_2H_5)_2$, $(C_2H_5)_2(CH_3)SiOAl(CH_3)(C_2H_5)$ and $(C_2H_5)_3SiOAl(CH_3)_2$.

The triethyl dimethyl siloxalane prepared by the process of the present invention will normally be used in the form obtained using the process. For instance the product of the process may be fed as a co-catalyst to a process for the polymerization of alpha-olefins, as is described in the aforementioned application of M. A. Hamilton et al.

The invention is illustrated by the following examples.

EXAMPLE I 10 g of triethyl aluminum (88 mmoles) were added, at ambient temperature and in a dry nitrogen atmosphere, to a flask containing 6.5 g of octamethyltetracyclosiloxane (22 mmoles). The admixture containing octamethylcyclotetrasiloxane was stirred during addition of the triethyl aluminum. The molar ratio of triethyl aluminum to octamethylcyclotetrasiloxane in the resultant admixture was 4:1. The admixture was heated to 185° C. and maintained at that temperature for a period of two hours; the resultant reaction product was allowed to cool to ambient temperature.

A sample of the reaction product was analyzed using nuclear magnetic resonance (NMR) spectroscopy. The spectra obtained had the following characteristics:

$^{29}$Si (39.74 MHz)NMR—NOE Suppressed: major peak at δ=18.8 ppm with associated shoulders at 19.7 and 16.8 ppm, smaller peaks at δ=22.2, 9.2, 1.9, −0.4 and −42.2 ppm. δ=0 ppm for tetramethylsilane control.

For comparison the octamethylcyclotetrasiloxane reactant had an NMR spectrum with the following characteristics:

$^{29}$Si (39.74 MHz)NMR—NOE Suppressed: one major peak at δ=−20.6 ppm, tetramethylsilane control having δ=0 ppm.

Comparison of the $^{29}$Si NMR spectra with that of known siloxalanes indicated that the reaction product is triethyl dimethyl siloxalane.

The reaction product was shown to be an active co-catalyst, with a heat-treated titanium/vanadium catalyst, in the polymerization of ethylene.

EXAMPLE II

The procedure of Example I was repeated except that the admixture was heated to 165° C. for a period of two hours. The reaction product had an NMR spectrum with the same characteristics as the product of Example I.

The reaction product, which contained a smaller amount of triethyl dimethyl siloxalane than that of Example I, was shown to have a correspondingly lower activity as a co-catalyst in a polymerization process of the type described in Example I.

EXAMPLE III

The procedure of Example I was repeated except that the admixture was heated to 50° C. for a period of two hours. The reaction product had an NMR spectrum with the following characteristics: $^{29}$Si (39.74 MHz)NMR—NOE Suppressed: One major peak at δ=−20.6 ppm, trimethylsilane having δ=0 ppm.

This example shows that admixing of triethyl aluminum and octamethyltetrasiloxane under conditions described by P. Gloriod et al. in the aforementioned U.S. Pat. No. 3,969,332 does not result in the preparation of triethyl dimethyl siloxane. The admixture does however show catalytic activity as a co-catalyst in a polymerization process of the type described in Example I because of the presence of triethyl aluminum.

EXAMPLE IV

The procedure of Example I was repeated except that equimolar amounts of triethyl aluminum and octamethylcyclotetrasiloxane were admixed and the resultant admixture was maintained at 165° C. for two hours. The reaction product had an NMR spectrum with the following characteristics: $^{29}$Si (39.74 MHz)NMR—NOE Suppressed: major peaks at δ=20.3, 19.5 and −20.6 ppm, minor peaks at δ=10.6, 9.4, 7.7, 5.2, 3.0, 1.3, −4.2, −8.2, −11.7, −13.7, −14.6 and −26.4 ppm, trimethylsilane having δ=0 ppm.

The NMR spectrum is consistent with the reaction product being the ring opened product and not triethyl dimethyl siloxalane.

EXAMPLE V

An admixture of triethyl aluminum and octamethylcyclotetrasiloxane was prepared using the procedure of Example I. Cyclohexane was then added: the resultant solution was 0.76 molar in triethyl aluminum.

The solution was passed through a coil in a heating bath maintained at a temperature of 170°, 185° or 200° C. The hold-up time of the solution in the heated coil was varied between about 12 minutes and about 42 minutes.

Samples of the reaction product were analyzed using NMR spectra. It was found that all runs at 185° C. and at 200° C. (a total of 7 runs) resulted in the formation of high yields of triethyl dimethyl siloxalane. The reaction product of some runs (3 runs) was tested as a co-catalyst in the polymerization reaction of Example I and found to be active.

It was also found that runs at 170° C. (a total of 2 runs) resulted in the formation of relatively lower yields of triethyl dimethyl siloxalane.

I claim:

1. A process for the preparation of triethyl dimethyl siloxalane comprising the step of admixing octamethylcyclotetrasiloxane with triethyl aluminum at a temperature of from about 170° to about 250° C. for a period of at least about 10 minutes, the molar ratio of triethyl aluminum to octamethylcyclotetrasiloxane being at least about 3.9:1.

2. The process of claim 1 in which the molar ratio of triethyl aluminum to octamethylcyclotetrasiloxane is in the range of from about 3.9 to about 4.5:1.

3. The process of claim 2 in which octamethylcyclotetrasiloxane is admixed with triethyl aluminum in the absence of an organic solvent.

4. The process of claim 2 in which octamethylcyclotetrasiloxane and triethyl aluminum are admixed in the presence of an inert hydrocarbon solvent.

5. The process of claim 2 in which the process is operated as a continuous process.

6. The process of claim 2 in which the temperature is from about 180° to about 200° C.

7. The process of claim 2 in which the period of time is in the range of from about 20 to about 120 minutes.

* * * * *